United States Patent
Kocer et al.

(10) Patent No.: US 10,508,954 B2
(45) Date of Patent: Dec. 17, 2019

(54) TEMPERATURE DETECTING DEVICE FOR A GAS TURBINE POWER PLANT AND GAS TURBINE POWER PLANT COMPRISING SAID TEMPERATURE DETECTING DEVICE

(71) Applicant: ANSALDO ENERGIA SWITZERLAND AG, Baden (CH)

(72) Inventors: Guelru Kocer, Birr (CH); Ken Haffner, Baden (CH)

(73) Assignee: ANSALDO ENERGIA SWITZERLAND AG, Baden (CH)

( * ) Notice: Subject to any disclaimer, the term of this patent is extended or adjusted under 35 U.S.C. 154(b) by 97 days.

(21) Appl. No.: 15/669,183

(22) Filed: Aug. 4, 2017

(65) Prior Publication Data

US 2018/0038736 A1  Feb. 8, 2018

(30) Foreign Application Priority Data

Aug. 8, 2016  (EP) .................................. 16183168

(51) Int. Cl.
| | | |
|---|---|---|
| *G01J 5/00* | (2006.01) | |
| *G01J 5/08* | (2006.01) | |
| *G01N 25/72* | (2006.01) | |
| *G01J 5/04* | (2006.01) | |

(52) U.S. Cl.
CPC .......... *G01J 5/0088* (2013.01); *G01J 5/0014* (2013.01); *G01J 5/041* (2013.01); *G01J 5/042* (2013.01); *G01J 5/046* (2013.01); *G01J 5/048* (2013.01); *G01J 5/0806* (2013.01); *G01J 5/0821* (2013.01); *G01J 5/0887* (2013.01); *G01N 25/72* (2013.01)

(58) Field of Classification Search
CPC ........ G01J 5/0014; G01J 5/0088; G01J 5/042; G01J 5/0821; G01J 5/0887; G01J 5/08; G01J 5/041; G01J 2005/0048; G01N 25/72; G01K 1/14; G01K 2205/00; G01K 13/00; G01K 13/02; G01K 2013/024; C10N 2240/10; C10N 2240/104
USPC ....... 374/141, 144, 130, 161, 137, 1, 2, 131, 374/166, 124; 356/43, 44
See application file for complete search history.

(56) References Cited

U.S. PATENT DOCUMENTS

| | | | | |
|---|---|---|---|---|
| 1,506,487 A | * | 8/1924 | Hutchings | H01R 33/973 439/303 |
| 3,137,134 A | * | 6/1964 | Macherey | F22B 1/22 110/162 |
| 4,666,245 A | | 5/1987 | Pointer | |

(Continued)

FOREIGN PATENT DOCUMENTS

| | | |
|---|---|---|
| EP | 0 898 158 A2 | 2/1999 |
| EP | 1 835 270 A1 | 9/2007 |

(Continued)

OTHER PUBLICATIONS

Search Report dated Feb. 6, 2007, by the European Patent Office for Application No. 16183168.0.

*Primary Examiner* — Gail Kaplan Verbitsky
(74) *Attorney, Agent, or Firm* — Buchanan Ingersoll & Rooney PC

(57) ABSTRACT

A temperature detecting device for a gas turbine power plant is provided with at least one optical probe configured to detect a parameter indicative of a temperature and with at least one capsule configured to define a camera inside which the optical probe is housed.

13 Claims, 3 Drawing Sheets

(56) References Cited

U.S. PATENT DOCUMENTS

| | | | |
|---|---|---|---|
| 4,770,544 A | 9/1988 | Mossey | |
| 5,078,507 A * | 1/1992 | Koller | G01J 5/0014 |
| | | | 374/131 |
| 5,364,186 A * | 11/1994 | Wang | G01J 5/04 |
| | | | 374/126 |
| 5,615,953 A | 4/1997 | Moskal | |
| 6,109,783 A | 8/2000 | Dobler et al. | |
| 6,698,920 B1 * | 3/2004 | Maylotte | G01J 5/0022 |
| | | | 356/73 |
| 2006/0146909 A1 * | 7/2006 | Morse | G01J 3/1895 |
| | | | 374/130 |
| 2010/0290733 A1 * | 11/2010 | Xia | F01D 17/085 |
| | | | 385/12 |
| 2011/0282501 A1 * | 11/2011 | Martin | F01D 19/00 |
| | | | 700/287 |
| 2013/0308680 A1 * | 11/2013 | Zhou | G01K 11/3206 |
| | | | 374/161 |
| 2015/0204732 A1 * | 7/2015 | Honda | B22D 11/124 |
| | | | 374/161 |
| 2015/0233771 A1 * | 8/2015 | Uno | G01K 11/3206 |
| | | | 374/4 |
| 2018/0340441 A1 * | 11/2018 | Miyamoto | F01D 11/22 |

FOREIGN PATENT DOCUMENTS

| | | |
|---|---|---|
| GB | 2 149 936 A | 6/1985 |
| WO | WO 2009/135814 A1 | 11/2009 |

* cited by examiner

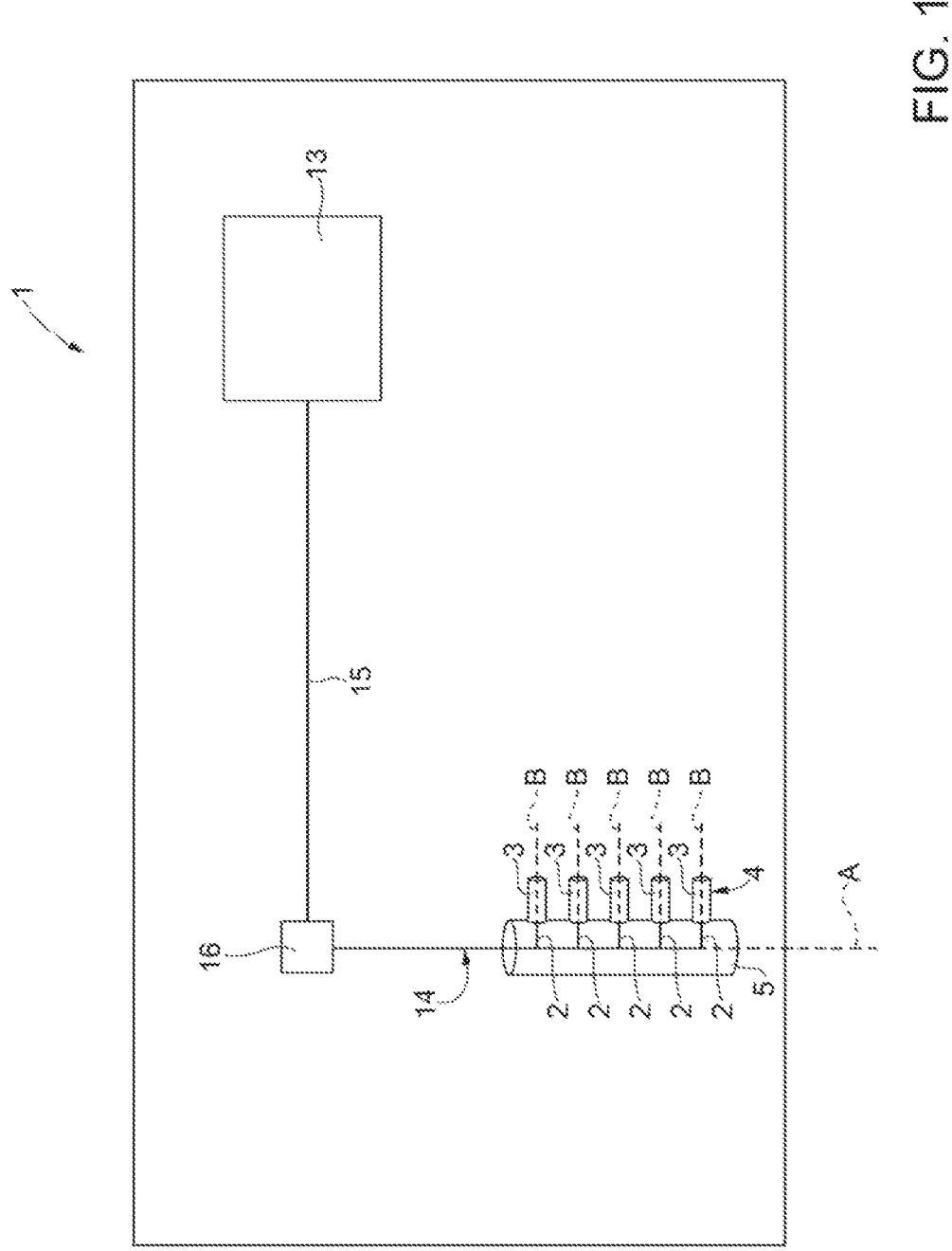

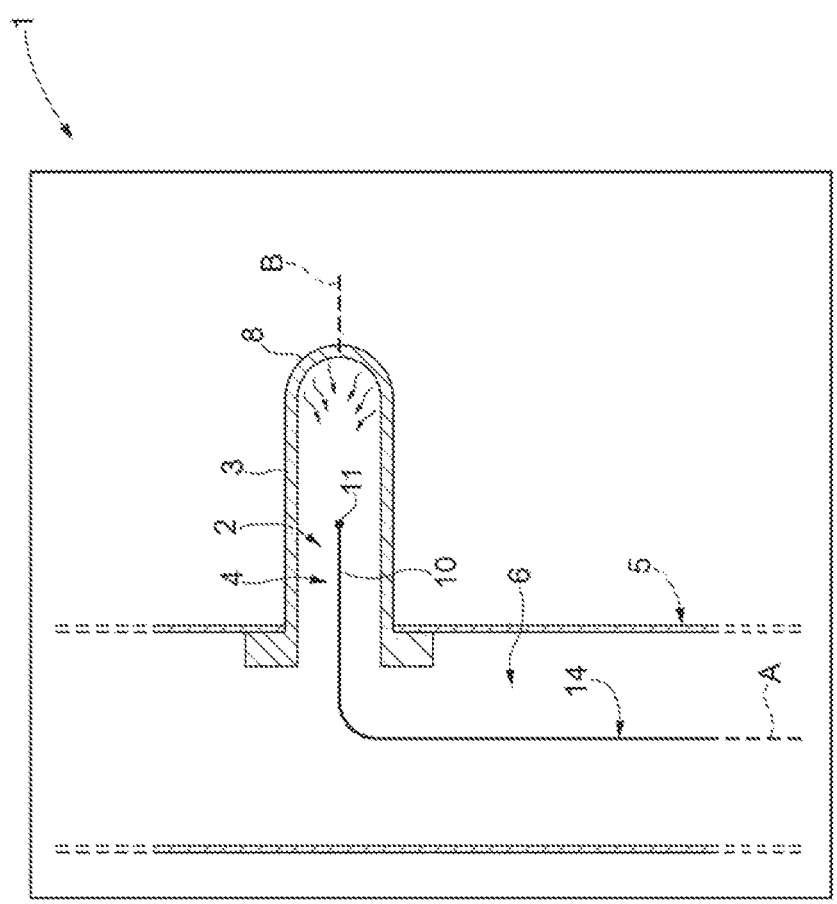

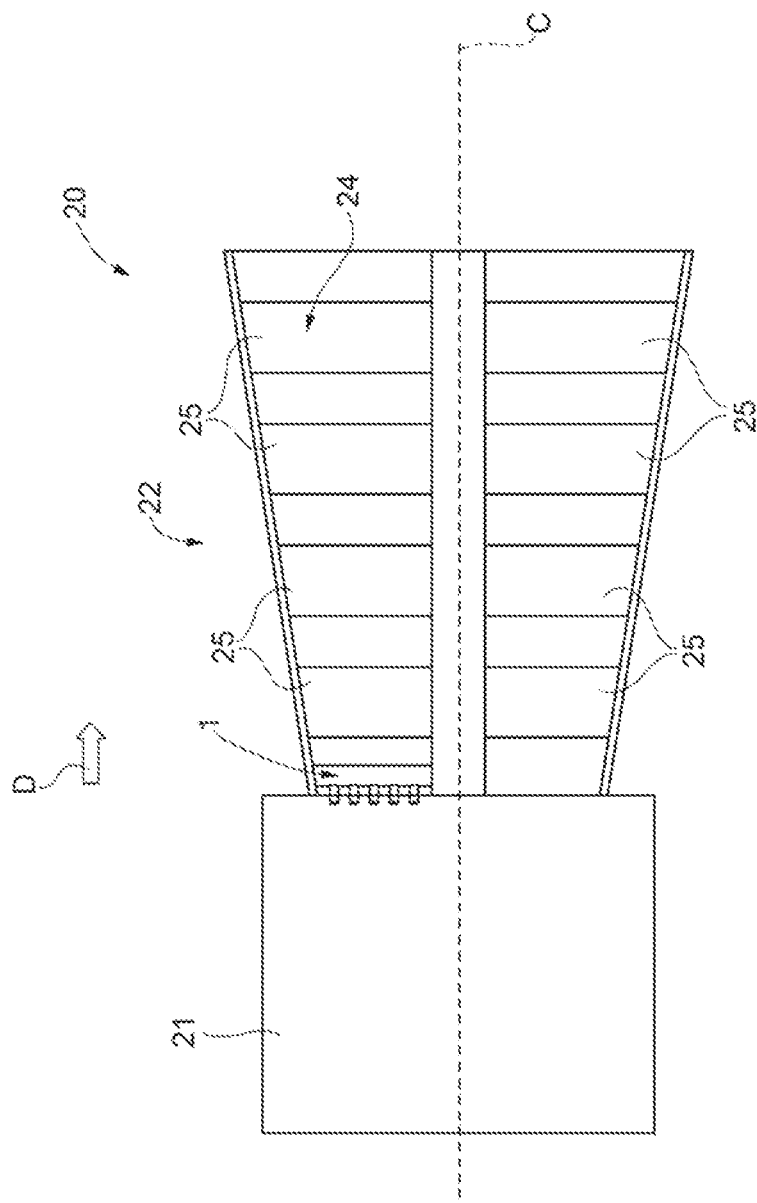

TEMPERATURE DETECTING DEVICE FOR A GAS TURBINE POWER PLANT AND GAS TURBINE POWER PLANT COMPRISING SAID TEMPERATURE DETECTING DEVICE

TECHNICAL FIELD

The present invention relates to a temperature detecting device for a gas turbine plant and to a gas turbine plant comprising said temperature detecting device.

BACKGROUND OF THE INVENTION

In known gas turbine power plants, temperature detecting devices are arranged at the outlet of the combustion chamber to control the temperature reached by the hot gases after the combustion.

The temperature detecting devices used in these plants comprise thermocouples.

However, thermocouples cannot withstand the temperature values reached in the gas turbine plant of the new generation. Thermocouples are made of alloys, for example Pt—Rh alloys, which melt at the operative temperature of the new gas turbine plant.

SUMMARY OF THE INVENTION

An object of the present invention is therefore to provide a temperature detecting device for a gas turbine power plant that enables avoiding, or at least mitigating, the described drawbacks.

In particular, it is an object of the present invention to provide a temperature detecting device for a gas turbine power plant reliably and, at the same time, sufficiently accurate.

According to the present invention, there is provided a temperature detecting device for a gas turbine power plant comprising
at least one optical probe configured to detect a parameter indicative of a temperature;
at least one capsule configured to define a camera inside which the optical probe is housed.

In this way the temperature detecting device is able to detect the temperature in gas turbine plants of the last generation. The capsule, in fact, is able to protect the sensing optical probe and, at the same time, to guarantee a good transmission of the temperature. The capsule, in fact, acts as a black body and emits inside the camera infra-red radiations depending on the temperature external to the capsule. The sensing optical probe detects the infra red radiations inside the camera.

Advantageously the components of the sensing optical probe are completely immune from the most common disorder of factors that affect thermocouples, as for example Radio-Frequencies, Micro Waves, Electromagnetic Fields, Nuclear radiation, Light Radiations.

Optical probes are also inherently safe because they are not current-carrying and therefore cannot generate sparks. They are non-flammable, resistant to chemicals, rust and corrosion.

Moreover also the dimensions of the optical probes are often of small size.

Optic systems for temperature measurement can also guarantee high accuracies (0.15° C.) and measuring frequencies up to 1000 Hz (i.e. a measurement every 0.02 seconds).

Finally, optical probes for sensing temperature are long-term stable and retain their accuracy for many years. When required, recalibration is simple and fast.

According to a preferred embodiment of the present invention, the optical probe comprises at least one optical fiber provided with a tip which is configured to collect the radiations inside the camera of the capsule; the capsule acting as a black body. In this way the Infra red radiation is detected by the tip of an optical fiber.

According to a preferred embodiment of the present invention the capsule is made of refractory material, preferably of ceramic material. In this way the capsule is able to withstand high temperatures and at the same time to act as a black body. The ceramic material, in particular, has a very high-temperature resistance.

According to a preferred embodiment of the present invention the device comprises a data acquisition unit coupled, directly or indirectly, to the optical fiber; the data acquisition unit being configured to transform the radiations collected by the optical fiber into temperature data. In this way the data acquired are collected in one single common unit.

According to a preferred embodiment of the present invention the device comprises a plurality of optical probes and a plurality of capsules each of which is configured to define a camera inside which a respective optical probe is housed.

In this way the temperature is detected by a plurality of sensing probes in order to improve the reliability of the detection.

According to a preferred embodiment of the invention the plurality of capsules are arranged side by side. In this way the temperature is detected along a definite direction in order to detect the spatial temperature distribution at defined locations. This feature is particularly useful when the detecting device is positioned in the hot gas flow path of a turbine in a gas turbine power plant.

According to a preferred embodiment of the invention each optical probe comprises at least one optical fiber provided with a tip; the plurality of optical fibers are coupled to a main optical fiber. The device comprising a data acquisition unit coupled, directly or indirectly, to the main optical fiber; the data acquisition unit being configured to transform the radiations collected by the main fiber into temperature data. In this way the data acquired by all the sensing probes are collected in one single common unit.

According to a preferred embodiment of the invention the temperature detecting device comprises a connecting optical fiber which has one end coupled to the data acquisition unit and the other end coupled to the main optical fiber by means of an adapter configured to couple the main optical fiber to the connecting optical fiber.

In this way, the connecting optical fiber and the main optical fiber can have different properties. For example, the main fiber, which normally runs in a hot environment, can be temperature resistant and therefore expensive, whereas the connecting optical fiber, which runs in a cold environment for a longer path can be of inferior quality and therefore cheaper than the main optical fiber.

The adapter is therefore useful for connecting optical fibers having different properties.

According to a preferred embodiment of the invention the temperature detecting device comprises a main body which is configured to support the plurality of capsules and is shaped so as to define a main camera which houses at least a portion of the main optical fiber; wherein the capsules protrudes perpendicularly from the main body.

In this way the main body is a sort of "rake body" configured to support the capsules in a specific way which optimizes the temperature detection.

It is another object of the present invention to provide a gas turbine power plant wherein the temperature is detected in a reliable and accurate way.

According to the present invention, there is provided a gas turbine power plant comprising:
- a compressor
- at least one combustion chamber;
- a turbine extending along a longitudinal axis and connected to the at least one combustion chamber; the turbine comprising an expansion channel wherein a hot gas flow flows along a main direction; and
- at least one temperature detecting device comprising at least one optical probe configured to detect a parameter indicative of a temperature and at least one capsule configured to define a camera inside which the optical probe is housed.

Thanks to the presence of an optical probe for detecting the temperature, the temperature is detected in a reliable and accurate way.

According to a preferred embodiment of the present invention the temperature detecting device is arranged at the inlet of the turbine facing upstream the hot gas flow. Preferably, the temperature detecting device is arranged so as the capsule inside which is housed the optical probe faces upstream the hot gas flow. In other words, the temperature detecting device is positioned at the inlet of the turbine so as the capsule is positioned counter current with respect to the main direction of the hot gas flow flowing in the expansion channel of the turbine.

According to a preferred embodiment of the present invention the turbine comprises a plurality of stages which are spaced along the longitudinal axis; each stage comprising fixed and rotating blades; the temperature detecting device being arranged in the expansion channel upstream the plurality of stages.

In this way the temperature of the hot gases is detected at the beginning of the expansion channel.

According to a preferred embodiment of the present invention the combustion chamber comprises an outlet channel; the temperature detecting device being arranged at the outlet channel facing upstream the hot gas flow.

BRIEF DESCRIPTION OF THE DRAWINGS

The present invention will now be described with reference to the accompanying drawings, which illustrate some non-limitative embodiment, in which:

FIG. 1 is a schematic representation of the temperature detecting device according to the present invention;

FIG. 2 is a schematic representation of a detail of the temperature detecting device of the FIG. 1;

FIG. 3 is a schematic representation of a portion of a power plant according to the present invention.

DETAILED DESCRIPTION OF THE INVENTION

Reference number 1 in FIG. 1 indicate a temperature detecting device according to the present invention.

The temperature detecting device 1 comprises at least one optical probe 2 configured to detect a parameter indicative of a temperature; and at least one capsule 3 configured to define a camera 4 inside which the optical probe 2 is housed.

In the non limiting example herein described and illustrated, the temperature detecting device 1 comprises a plurality of optical probes 2 and a plurality of capsules 3 and a main body 5 configured to support the plurality of capsules 3. The capsules 3 protrude from the main body 5.

Preferably the optical probes 2 of the plurality of optical probes and the capsules 3 of the plurality of capsules are identical one to the other.

A variant not shown provides that the optical probes of the plurality of optical probes have different properties and/or dimensions and that the capsules of the plurality of capsules have, according to the features of the respective optical probes, different properties and/or shape.

With reference to FIG. 1 and FIG. 2, the main body 5 extends along a main axis A. In the non limiting example herein described and illustrated, the main body 5 supports the capsules 3 orthogonally to the main axis A. However, according to variants not shown the capsules 3 can be supported by the main body 5 not orthogonally to the main axis A.

The main body 5 is a hollow body shaped so as to define a main camera 6.

In the non limiting example here described and illustrated the main body 5 is a cylindrical body and the main camera 6 is in communication with the cameras 4 of the capsules 3.

The main body 5 is preferably made of the same material of the capsules 3. The main body 5 and the capsules 3 are preferably integral with one another.

Each capsule 3 is made of refractory material, preferably is made of ceramic material.

In the non limiting example here described and illustrated each capsule 3 is made of a material comprising alumina.

Preferably, each capsule 3 is defined by a body having a cylindrical or conical shape open at the end coupled to the main body 5 and closed at the opposite end with a dome-shaped element 8.

Each optical probe 2 comprises at least one optical fiber 10 provided with a tip 11.

As hinted before, each optical probe 2 is arranged inside the respective camera 4.

In particular, each optical probe 2 is arranged inside the respective camera 4 so as the tip 11 of the fiber 10 is arranged substantially on the centre line of the camera 4.

Preferably each optical probe 2 extends along the axis B of the respective capsule 3.

The tip 11 is configured to collect the radiation in the camera 4.

Preferably, the optical fiber 10 is a sapphire optical fiber.

The plurality of optical fibers 10 are connected, directly or indirectly, to a data acquisition unit 13, which communicates the detected data to a control system (not illustrated in the enclosed drawings).

In particular, the data acquisition unit 13 is configured to calculate an average temperature on the basis of the radiations coming from the optical probes 2. Advantageously, as the temperature detecting device 1 comprises a plurality of probes 2, the detection of the temperature is more reliable as there are redundant probes and more accurate as the temperature is calculated as the average of the plurality of temperature detections.

In the non limiting example here described and illustrated each fiber 10 is connected to a main optical fiber 14.

The main optical fiber 14 is partially housed inside the main camera 6 of the main body 5 and is coupled to a connecting optical fiber 15 by means of an adapter 16.

The adapter 16 is an optical connector configured to couple the main optical fiber 14 to the connecting optical fiber 15.

Main optical fiber 14 and connecting optical fiber 15 have preferably different properties.

The main optical fiber, which normally runs in a hot environment, can be temperature resistant and therefore expensive, whereas the connecting optical fiber, which runs in a cold environment for a longer path can be of inferior quality and therefore cheaper than the main optical fiber. The connecting optical fiber 15 has one end coupled to the data acquisition unit 13 and the other end coupled to the main optical fiber 14, and in particular to the adapter 16.

Preferably, the main optical fiber 14 is a sapphire optical fiber, while the connecting optical fiber 15 has a silica based core and a silica based cladding.

In use, each capsule 3 acts as a black body.

In other words each capsule 3 absorbs the heat to which it is exposed and emits infra-red radiations in the camera 4 depending on the external temperature of the capsule 3.

In this way the IR radiations (schematically represented by the arrows in FIG. 2) emitted inside the camera 4 are indicative of the temperature outside the respective capsule 3.

The optical probe 2, and in particular the tip 11, detects the IR radiation inside the respective camera 4.

All the radiations detected by each optical probe 2 are sent to the data acquisition unit 13 as described before. The data acquisition unit 13 transforms the radiations into data.

In FIG. 3 is schematically represented a portion of a gas turbine power plant 20 according to the present invention.

The gas turbine power plant comprises a compressor (not illustrated) at least one combustion chamber 21, a turbine 22 connected to the combustion chamber 21 and at least one temperature detecting device 1.

The turbine 22 extends along a longitudinal axis C and comprises an expansion channel 24 and a plurality of stages 25 which are spaced along the longitudinal axis C; each stage 25 comprises fixed and rotating blades (not illustrated).

In the embodiment illustrated in FIG. 3 the temperature detecting device 1 is arranged in the expansion channel 24 upstream the plurality of stages 25 wherein flows a hot gas flow along a main direction D (indicated by an arrow in FIG. 3).

In particular, the temperature detecting device 1 faces upstream the hot gas flow.

Preferably, the temperature detecting device 1 is arranged so as each capsule 3 inside which is housed the respective optical probe 2 faces upstream the hot gas flow.

In other words, the temperature detecting device 1 is positioned at the inlet of the turbine 22 so as each capsule 3 is positioned counter current with respect to the main direction of the hot gas flow flowing in the expansion channel of the turbine.

In the non limiting example here described and illustrated, the capsules 3 are orthogonal to the main body 5. However, the capsules 3 could also be arranged in various directions, along curved lines or following different flow angles within the hot gas flow.

In the non limiting example here described and illustrated, the temperature detecting device 1 is arranged inside the expansion channel 24 so as the main axis A of the main body 5 is arranged radially with respect to the longitudinal axis C of the gas turbine. However variants not shown provide that the main body is not radially arranged.

Preferably the temperature detecting device 1 is fixed to the stator casing of the gas turbine 22.

A variant not shown provides that the temperature detecting device 1 is arranged at the outlet channel (not shown) of the combustion chamber 21.

Finally, it is clear that modifications and variants can be made to the device and the plant described herein without departing from the scope of the present invention, as defined in the appended claims.

The invention claimed is:

1. Temperature detecting device for a gas turbine power plant, the temperature detecting device comprising:
   at least one optical probe configured to detect a parameter indicative of a temperature;
   at least one capsule configured to define a camera inside which the optical probe is housed;
   a plurality of optical probes and a plurality of capsules, each capsule configured to define a camera inside which a respective optical probe is housed, each optical probe having an optical fiber with a tip configured to collect radiations inside the camera of the capsule, wherein at least one of the plurality of capsules is a black body; and
   a main body configured to support the plurality of capsules and shaped to define a main camera which houses at least a portion of a main optical fiber,
   wherein each optical fiber of the plurality of optical probes extends into the main body and connects to the portion of the main optical fiber housed in the main body along a respective probe axis that is not parallel with the main axis of the main body, the main optical fiber extends along a main axis of the main body, and each optical fiber of the plurality of optical probes extends along the respective probe axis.

2. Device according to claim 1, wherein the capsule of each optical probe is a black body.

3. Device according to claim 1, wherein at least one of the plurality of capsules is made of refractory material.

4. Device according to claim 2, comprising:
   a data acquisition unit coupled, directly or indirectly, to the optical fiber, the data acquisition unit being configured to transform the radiations collected by the optical fiber into temperature data.

5. Device according to claim 1, wherein the plurality of capsules are arranged side by side.

6. Device according to claim 1, comprising:
   a data acquisition unit coupled, directly or indirectly, to the main optical fiber, the data acquisition unit being configured to transform radiations collected by the main optical fiber into temperature data.

7. Device according to claim 6, comprising:
   a connecting optical fiber which has one end coupled to the data acquisition unit and another end coupled to the main optical fiber.

8. Device according to claim 7, comprising:
   an adapter configured to couple the main optical fiber to the connecting optical fiber.

9. Device according to claim 1, wherein each capsule is made of ceramic material.

10. Gas turbine power plant comprising:
    a compressor;
    at least one combustion chamber;
    a turbine extending along a longitudinal axis (C) and connected to the at least one combustion chamber, the turbine including an expansion channel wherein a hot gas flow flows along a main direction (D);

at least one temperature detecting device disposed in the expansion channel, the at least one temperature detecting device having:

at least one optical probe configured to detect a parameter indicative of a temperature, and at least one capsule configured to define a camera inside which the optical probe is housed;

a plurality of optical probes and a plurality of capsules, each capsule defines a camera inside which a respective optical probe is housed, each optical probe having an optical fiber with a tip configured to collect radiations inside the camera of the capsule; and a main body configured to support the plurality of capsules and shaped to define a main camera which houses at least a portion of a main optical fiber, wherein each optical fiber of the plurality of optical probes extends into the main body and connects to the portion of the main optical fiber housed in the main body along a respective probe axis that is not parallel with the main axis of the main body, the main optical fiber extends along a main axis of the main body, and each optical fiber of the plurality of optical probes extends along the respective probe axis.

11. Gas turbine power plant according to claim 10, wherein the temperature detecting device is arranged at an inlet of the gas turbine facing upstream a hot gas flow pathway.

12. Gas turbine power plant according to claim 11, wherein the turbine comprises:

a plurality of stages which are spaced along the longitudinal axis (C) in the expansion channel, each stage having fixed and rotating blades, the temperature detecting device being arranged in the expansion channel upstream the plurality of stages.

13. Gas turbine power plant according to claim 10, wherein the combustion chamber comprises:

an outlet channel, the temperature detecting device being arranged at the outlet channel facing upstream a hot gas flow pathway.

\* \* \* \* \*